United States Patent [19]
Volk

[11] Patent Number: 6,164,779
[45] Date of Patent: Dec. 26, 2000

[54] OPHTHALMOSCOPIC VIEWING SYSTEM

[75] Inventor: Donald A. Volk, Mentor, Ohio

[73] Assignee: Volk Optical, Inc., Mentor, Ohio

[21] Appl. No.: 09/091,772

[22] PCT Filed: Oct. 23, 1997

[86] PCT No.: PCT/US97/18963

§ 371 Date: Jun. 22, 1998

§ 102(e) Date: Jun. 22, 1998

[87] PCT Pub. No.: WO98/17170

PCT Pub. Date: Apr. 30, 1998

Related U.S. Application Data

[60] Provisional application No. 60/029,473, Oct. 24, 1996.

[51] Int. Cl.[7] .................................................. A61B 3/00
[52] U.S. Cl. ............................................................. 351/219
[58] Field of Search .................................. 351/200, 205, 351/212, 216–221; 606/4–6

[56] References Cited

U.S. PATENT DOCUMENTS

| | | |
|---|---|---|
| 5,200,773 | 4/1993 | Volk . |
| 5,359,372 | 10/1994 | Kida et al. . |
| 5,523,810 | 6/1996 | Volk ........................................ 351/219 |
| 5,537,164 | 7/1996 | Smith . |

FOREIGN PATENT DOCUMENTS

| | | |
|---|---|---|
| 2 301 468 | 8/1973 | Germany . |
| 2 101 349A | 1/1983 | United Kingdom . |

*Primary Examiner*—George Manuel
*Attorney, Agent, or Firm*—Venable; Robert Kinberg

[57] ABSTRACT

A gonioscopic viewing system is provided for diagnosis or laser treatment of the anterior chamber angle of a patient's eye. A first lens system includes a concave posterior lens surface with a shape substantially corresponding to the shape of an average cornea so that, when placed on a patient's eye, light rays originating at the anterior chamber angle and passing through the aqueous humor, pass through the cornea and the posterior lens surface of the first lens system and are directed by the first lens system toward an image forming system. An image forming system is optically aligned with the first lens system for capturing the light rays directed by the first lens system and focusses the light rays to form a real image of the anterior chamber angle outside of the patient's eye.

39 Claims, 10 Drawing Sheets

OPHTHALMOSCOPIC VIEWING SYSTEM

This application is a 371 of PCT/US97/18963 filed Oct. 23, 1997 and also claims the benefit of U.S. Provisional Application Ser. No. 60/029,473 filed Oct. 24, 1996.

BACKGROUND OF THE INVENTION

The present invention relates to ophthalmoscopic viewing systems for use with a slit lamp or other biomicroscope for diagnosis and/or treatment of structures within the eye, including, for example, the fundus, the anterior chamber angle, iris and ciliary process. In particular, the invention relates to ophthalmoscopic viewing systems for creating a real image outside the eye of structures within the eye.

Special ophthalmoscopic lenses have been developed for viewing structures within the eye for purposes of diagnosis and/or other surgical treatment of the eye. For example, indirect ophthalmoscopic lenses are known which produce a real image of a patient's fundus outside of the eye for use with a slit lamp or other biomicroscope. Direct ophthalmoscopic lenses are also known which produce a virtual image within the eye of the patient's fundus which can be viewed by the physician. Generally speaking, the virtual image produced by a direct ophthalmoscopic lens has a higher magnification than the real image produced by an indirect ophthalmoscopy lens, but has a smaller field of view. The virtual image produced by an direct ophthalmoscopic lens is a true, upright image. The real image produced by an indirect ophthalmoscopic lens is inverted and reversed, so that either the physician must learn to work with the inverted and reversed image or special measures must be taken to convert the initial real image produced by the indirect ophthalmoscopic lens to a true, upright image such as disclosed, for example, in U.S. Pat. No. 4,721,378 to David Volk. With the use of such additional measures, it is possible to employ an indirect ophthalmoscopic lens to observe a large field of view of a true and upright image of a patient's fundus.

Gonioscopic devices are available for viewing the anterior chamber angle of a patient's eye. Known devices, such as the Koeppe lens, employ a contact lens having a highly curved convex anterior lens surface. The contact lens, together with a tear layer between the cornea and the posterior surface of the contact lens, shifts the cornea-air interface to the highly curved anterior lens surface. Due to the more nearly normal (or perpendicular) light passage through the anterior surface, light rays originating at the anterior chamber angle pass through the front surface of the cornea, into the lens and out of the steeply curved anterior surface. Although the Koeppe lens produces a true and upright magnified image of the anterior chamber angle, the field of view is small and the physician is required to view the image at a highly off-axis position.

Mirrored gonioscopic lenses are known, such as the Goldmann lens, which employ an angulated mirror within the lens. The lens operates to eliminate the power of the cornea to avoid total reflection of the light rays at the cornea-air interface. Light rays from the anterior chamber angle enter the lens and are reflected by the mirror along the line of vision of the viewer. However, because of the mirror, the image of the angle is reversed and inverted. Additionally, like the Koeppe lens, the field of view is very small.

It would be desirable to have an ophthalmoscopic viewing system for viewing structures within the eye, including anterior structures such as the anterior chamber angle, iris and ciliary process, which has advantageous features of an indirect ophthalmoscopy lens, including the provision of a large field of view, so that the physician could observe an uninterrupted 360° annular ring of the iris and anterior chamber angle, and preferably view such an image in an upright and correctly oriented position.

It would further be desirable to provide for improved ophthalmoscopic viewing systems for producing a true and upright real image outside of the eye of structures within the eye, including the fundus, to facilitate diagnosis and treatment.

SUMMARY OF THE INVENTION

It is an object of the invention to provide improved ophthalmoscopic devices for viewing internal structures of the eye.

It is another object of the invention to provide a gonioscopic viewing system for use in diagnosis and laser treatment of the anterior chamber angle which produces a large field of view of the anterior chamber angle.

It is another object of the invention to provide a gonioscopic viewing system in which a true and correctly oriented real image of the anterior chamber angle can be viewed through a slit lamp or other biomicroscope.

It is still another object of the invention to provide ophthalmoscopic viewing systems which produce a true and correctly oriented image of internal structures of the eye, including the fundus.

The above and other objects are accomplished according to one aspect of the invention by the provision of a gonioscopic viewing system for diagnosis or laser treatment of the anterior chamber angle of a patient's eye, comprising: a first lens system including a concave posterior lens surface with a shape substantially corresponding to the shape of an average cornea so that, when placed on a patient's eye, light rays originating at the anterior chamber angle and passing through the aqueous humor, pass through the cornea and the posterior lens surface of the first lens system and are directed by the first lens system toward an image forming system; and an image forming system optically aligned with the first lens system for capturing the light rays directed by the first lens system and focussing the light rays to form a real image of the anterior chamber angle outside of the patient's eye.

According to one embodiment of the invention, the image forming lens system comprises a biconvex lens and the real image is formed anterior of the biconvex lens.

According to another feature of the invention, an anterior convex lens surface is disposed for bending the light rays passing through the concave posterior lens surface toward the biconvex lens. According to another aspect of the invention, the biconvex lens is spaced from the anterior convex lens surface.

In order to further converge the light rays toward the biconvex lens, an intermediate meniscus shaped lens may be positioned between the convex anterior lens surface and the biconvex lens.

According to yet another aspect of the invention, an upright and true real image of the anterior chamber angle is created by arranging first and second light reflecting surfaces, one of which is curved, optically in series for reflecting and focussing the light rays captured by the image forming system, thereby producing an intermediate real image which is inverted and reversed, and utilizing the biconvex lens anterior of the reflecting surfaces for capturing and focussing the light rays forming the intermediate real image to form an upright and true real image of the anterior chamber angle.

The curved reflecting surface is advantageously concave and arranged to reflect the light rays in a posterior direction, while the other reflecting surface is disposed posterior of the concave reflecting surface for reflecting light rays from the concave reflecting surface for reflecting light rays from the concave reflecting surface in an anterior direction to the form the intermediate real image. In this embodiment, the other reflective surface may be planar, concave or symmetrically shaped with respect to the one concave reflecting surface.

According to yet another embodiment of the invention, third and fourth reflecting surfaces are provided for reflecting light from the intermediate real image to form the upright and true real image anterior of the biconvex lens. In this embodiment, the anterior and posterior surfaces of the biconvex lens are partially mirrored for providing the third and fourth reflecting surfaces.

In yet another embodiment of the invention, the image forming system is provided by an ellipsoidal reflecting surface for reflecting the light passing through the posterior lens surface of the first lens system generally toward a focus of the ellipsoidal surface to form a conjugate pupil region of the patient's eye and another reflecting surface is provided in the form of a parabolic reflecting surface for reflecting light emanating from the conjugate pupil region to form the real image.

According to still another embodiment of the invention, one of the reflecting surfaces comprises a central convex reflecting surface and another reflecting surface comprises a concave reflecting surface having a plus optical power disposed around the central convex reflecting surface for reflecting and focussing the light rays passing through the posterior lens surface of the first lens system toward the central convex reflecting surface which in turn reflects and focuses the light to form the real image. In this embodiment, the real image is produced within the system rather than in air anterior to the system. Additionally, although the image is not upright and correctly oriented as in other embodiments, the magnification of the image is such as to size and extent to allow the entire annular shaped image of the anterior chamber angle to be seen in a single view.

In the course of developing the two and four mirror embodiments mentioned above for producing a real image of the anterior chamber angle outside of the eye, Applicant has discovered that by appropriately choosing the surface characteristics of the reflecting and refracting surfaces, the novel mirrored systems, originally developed for viewing the anterior chamber angle, may be utilized for producing a real image of the fundus outside the eye. That is, the novel mirrored systems which were developed specifically for producing a real image outside of the eye and to thus incorporate the advantageous characteristics of an indirect ophthalmoscopy lens can, with appropriate choices of the surface characteristics of the reflecting and refracting surfaces, result in an improved indirect ophthalmoscopy lens for observing the fundus. With suitable modifications to the surface characteristic, the mirrored system disclosed herein may additionally be utilized to produce real images of the iris and ciliary process which can be viewed through a biomicroscope for purposes of diagnosis and laser treatment.

DETAILED DESCRIPTION OF THE INVENTION

Figure 1:
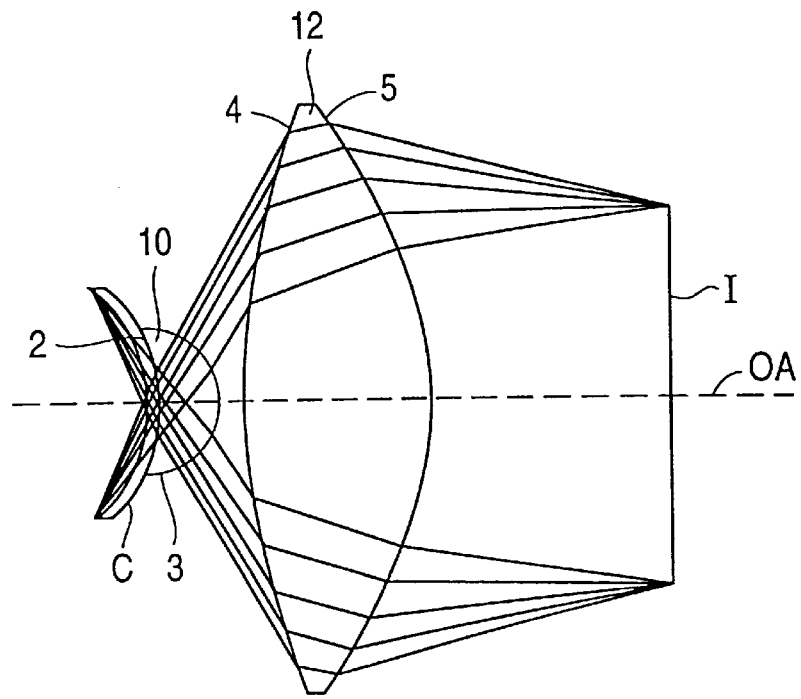
FIG. 1 is a schematic side sectional view of a gonioscopic viewing system, together with a ray tracing, according to one embodiment of the invention.

Referring to FIG. 1, there is shown a schematic side sectional view of a lens layout of a gonioscopic viewing system according to a first embodiment of the invention, overlaid with a ray tracing showing the path of light rays emanating from the anterior chamber angle of the eye and passing through the aqueous humor, cornea and then through the viewing system for producing a real image of the anterior chamber angle outside the eye. In FIG. 1, the gonioscopic viewing system includes a contact lens element 10 and a biconvex lens 12 disposed anterior of the contact lens element. In practice, contact lens element 10 and biconvex lens 12 are fixedly and coaxially mounted with respect to one another in a frame which is not shown for ease of illustration, which is the case for all of the figures herein. Contact lens element 10 has a concave posterior surface 2 with a curvature substantially corresponding to that of an average cornea C on which contact lens element 10 is placed in operation. Contact lens element 10 has a convex anterior surface 3 which is preferably spherical. Biconvex lens 12 has a convex posterior surface 4 and a convex anterior surface 5.

Advantageously, one or both of the surfaces 4 and 5 are asymmetric in order to optimally maintain high resolution and image clarity with large pupil diameters. The formula $$z = \frac{cr^2}{1 + \sqrt{1-(1+k)c^2r^2}} + a_1r + a_2r^2 + a_3r^3 \ldots a_nr^n$$

has been utilized in defining the aspheric surfaces of this invention, where z equals the surface sag along the lens axis, c equals the curvature (i.e., reciprocal of the radius), r is the radial coordinate in lens units, k equals the conic constant, and $a_n$ (where n=1,2, ... ) is the coefficient value of any of the selected conic deformation terms. Tailoring of any of the lens surfaces of this invention through the use of coefficient terms may be accomplished as desired.

In an exemplary construction of the gonioscopic viewing system illustrated in FIG. 1, contact lens element 10 is made of acrylic, for example, polymethylmethacrylate (PMMA), which has an index of refraction of 1.49, and biconvex lens 12 is made of LAH-58 Lanthanum glass manufactured by O'Hara Corporation having an index of refraction of 1.883.

In the exemplary construction, concave posterior surface 2 has an 8.0 mm apical radius which is somewhat steeper than the average corneal radius of 7.7 mm. As a result, there is a small separation between the cornea C and concave posterior surface 2 of approximately 0.05 mm which is filled with a tear layer having an index of refraction corresponding to that of the cornea, which is approximately 1.376. In this exemplary construction, anterior surface 3 has a 4 mm radius of curvature and is separated along the apical axis from posterior surface 2 by 3.5 mm. Contact element 10 has a diameter of 8.0 mm. Biconvex lens 12 is spaced from contact lens element 10 along the apical axis by a distance of 1.8 mm. Convex posterior surface 4 has an apical radius of 20.67629 mm with a conic constant k of −9.866896. Anterior convex surface 5 of biconvex lens 12 has an apical radius of −17.49772 and a conic constant k of −0.3988085, with a sixth order coefficient in the above formula of $7.576656e^{-008}$. Biconvex lens 12 has a diameter of 31 mm and a thickness along the apical axis of 10.86 mm.

The following Table 1 summarizes the surface data for the above exemplary construction of the embodiment of FIG. 1.

TABLE 1

(FIG. 1)

| Surface No. | Apical Radius (r) | Conic Constant (k) | Diameter (mm) | Spacing from Apex of Posterior Contact Surface (mm) |
| --- | --- | --- | --- | --- |
| 2 | −8.0 | 0 | 8.0 | 0 |
| 3 | −4.0 | 0 | 8.0 | 3.5 |
| 4 | 20.67629 | −9.866896 | 31.0 | 5.3 |
| 5 | −17.49772 | −0.3988085 | 31.0 | 16.16 |

In the above Table 1 and the following tables providing summary surface data for other embodiments of the invention, the Radius (r) column indicates the apical radius of the corresponding surface, which is the radius of the surface at the point where the surface or an imaginary continuation of the surface crosses the optical axis OA. A positive radius indicates that a curved surface opens toward the anterior direction, i.e., away from the eye and a negative radius indicates that a curved surface opens toward the posterior direction, i.e., toward the eye. This convention is used throughout this specification. In accordance with the usual convention, a 0 Conic Constant (k) denotes a spherical surface, a negative conic constant indicates a conical surface which flattens out toward the periphery and a positive conic constant indicates a conical surface that becomes more steep toward the periphery. In the table and throughout this specification, the surfaces mentioned in the exemplary constructions are all pure conics unless higher order deformation terms with respect to the foregoing formula are specifically mentioned. The Diameter of the surface is the distance from edge to edge of the respective surface. The column labelled Spacing from Apex of Posterior Contact Surface utilizes the apex of the concave posterior contact surface 2A as the "0" point along the optical axis OA so that the spacing of all surfaces are relative to this 0 point. The spacing indicates the distance of the apex of a surface, i.e., the point at which the surface, or an imaginary continuation of the surface crosses the optical axis, from the 0 point. The relative spacing between any two surfaces may be obtained by subtracting the corresponding spacings indicated in the table. For example, the distance between the apex of surface 4 and the apex of surface 5 is 10.86 mm (i.e., 16.16 mm−5.3 mm=10.86 mm).

When a gonioscopic viewing system according to the above exemplary construction of FIG. 1 is placed on a normal eye, light rays emanating from the anterior chamber angle, where the iris meets the cornea, will proceed through the aqueous humor (index of refraction equal to 1.336), through the cornea (index of refraction equal to 1.376) and into the contact lens element 10 which is in place on cornea C. The light rays proceed through contact lens element 10 into air before entering biconvex lens 12 and being focussed as a real, aerial image in a plane I anterior to the viewing system. With the above-mentioned exemplary construction, a real image of the anterior chamber angle will be formed at 11.46 mm from the apex of convex anterior surface 5. In the gonioscopic viewing system according to the embodiment of FIG. 1, the aerial image is reversed and inverted in a manner similar to indirect ophthalmoscopy.

It should be understood that although one anterior biconvex lens is shown, one or more anterior elements may be utilized to provide a real image of the angle in accordance with the principles of this invention. For example, a middle, biconvex, plano/convex or concavo-convex lens may be utilized as will be understood by those skilled in the art.

Figure 2:
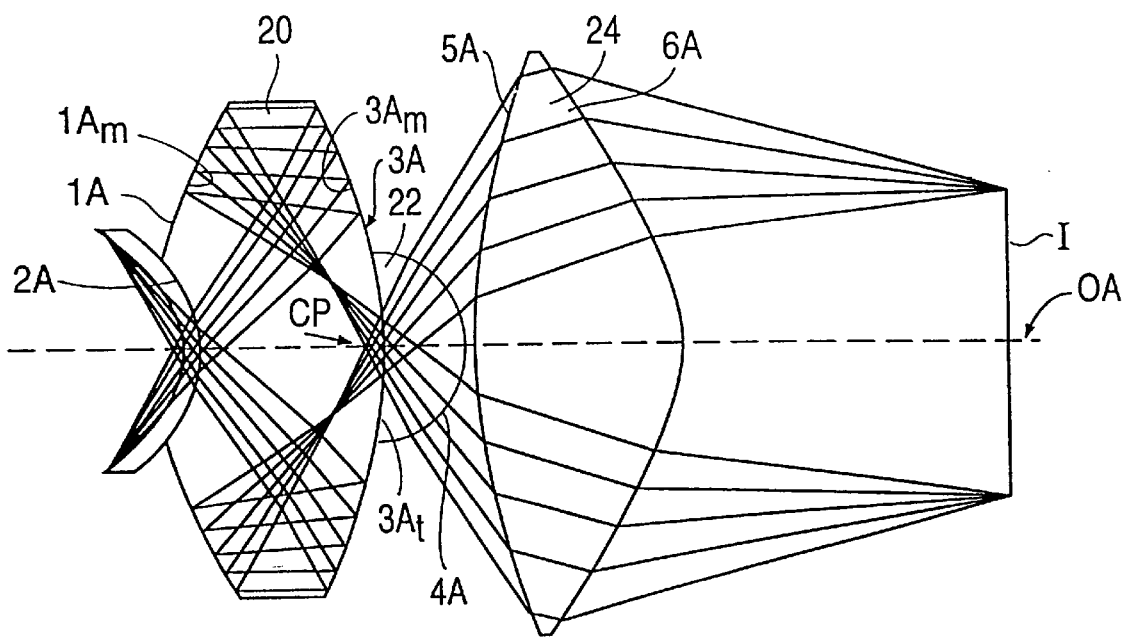
FIGS. 2 through 9 are schematic side sectional views of gonioscopic viewing systems incorporating mirrored systems for producing real images of the anterior chamber angle of the eye according to further embodiments of the invention.

FIG. 2 shows a gonioscopic viewing system according to another embodiment of the invention which employs a lens component having curved mirror surfaces together with a biconvex imaging lens to produce a true, upright, real aerial image of the anterior chamber angle. In accordance with this embodiment of the invention, a lens component 20 made of PMMA acrylic has a concave posterior surface 2A in a central region that is shaped similarly to concave posterior surface 2 in FIG. 1 to substantially match the curvature of the average cornea. Lens component 20 further includes a posterior convex surface 1A peripherally of concave posterior surface 2A that is provided with a reflective coating to produce a concave mirror surface $1A_m$ for reflecting and focussing incident light. Although convex posterior surface 1A terminates where it meets concave posterior surface 2A, an imaginary continuation of surface 1A in the region of optical axis OA is shown by a dashed line. Lens component 20 has a convex anterior surface 3A with an optically transmissive central region $3A_t$ and a peripheral region provided with a reflective coating to form a concave mirror surface $3A_m$ for reflecting and focussing incident light. Anterior surface 3A has a centrally disposed lens cap 22 with a posterior surface having a shape corresponding to that of surface 3A in its central transmissive region 3A$_t$ and being glued with an optical cement to surface 3A. Lens cap 22 presents a steeply curved convex anterior surface 4A. A biconvex lens 24 is spaced in an anterior direction from convex surface 4A and has a convex posterior surface 5A and a convex anterior surface 6A.

Mirrored surfaces 1A$_m$ and 3A$_m$ both have an aspheric concave shape. As shown by the overlaid ray tracing in FIG. 2, light rays originating at the anterior chamber angle and proceeding through the aqueous humor and cornea, pass through the central concave posterior surface 2A and proceed toward mirrored surface 3A$_m$ where they are reflected and focussed in a posterior direction toward mirrored surface 1A$_m$ from which they are again reflected and further focussed to form an inter-mediate real image of the angle within lens 20. The rays continue toward non-mirrored portion 3A$_t$ of anterior surface 3A to a conjugate pupil location CP where the chief rays cross one another and optical axis OA and proceed toward the convex surface 4A and exit into the air space between lens cap 22 and biconvex lens 24. The rays proceed through biconvex lens 24 which directs and focusses the rays to form a real aerial image anterior of the viewing system in a plane I. The viewing system according to FIG. 2 produces a fully continuous, upright and correctly oriented image of the anterior chamber angle.

In an exemplary construction of the embodiment shown in FIG. 2, lens 20 may comprise a double paraboloid biconvex lens made of PMMA acrylic which is mirrored in the peripheral areas on both external surfaces, and uncoated in the central areas to produce the peripheral mirrored areas and central transmitting areas as discussed above. The glued on lens cap is likewise made of PMMA acrylic. FIG. 2 shows the mating surfaces as being curved, with the central area of the anterior surface 3A defining the matching surface of cap 22. The matching surface radii of surface 3A and acrylic cap 22 may be concave, convex or flat. Biconvex lens 24 is made of LAH 58 glass.

A gonioscopic viewing system constructed in accordance with the exemplary surface data in Table 2 below will produce a real image of the anterior chamber of a normal eye at 15 mm anterior of surface 6A along optical axis OA.

TABLE 2

(FIG. 2)

| Surface No. | Apical Radius (r) | Conic Constant (k) | Diameter (mm) | Spacing from Apex of Posterior Contact Surface (mm) |
|---|---|---|---|---|
| 1A | 20.5 | −1.0 | 24.0 | −2.0 |
| 2A | −8.0 | 0 | 9.2 | 0 |
| 3A | −20.5 | −1.0 | 24.0 | 9.0 |
| 4A | −4.5 | 0 | 9.0 | 14.0 |
| 5A | 24.38787 | −5.279118 | 28.0 | 14.5 |
| 6A | −8.868317 | −2.639559 | 28.0 | 25.0 |

Figure 3:
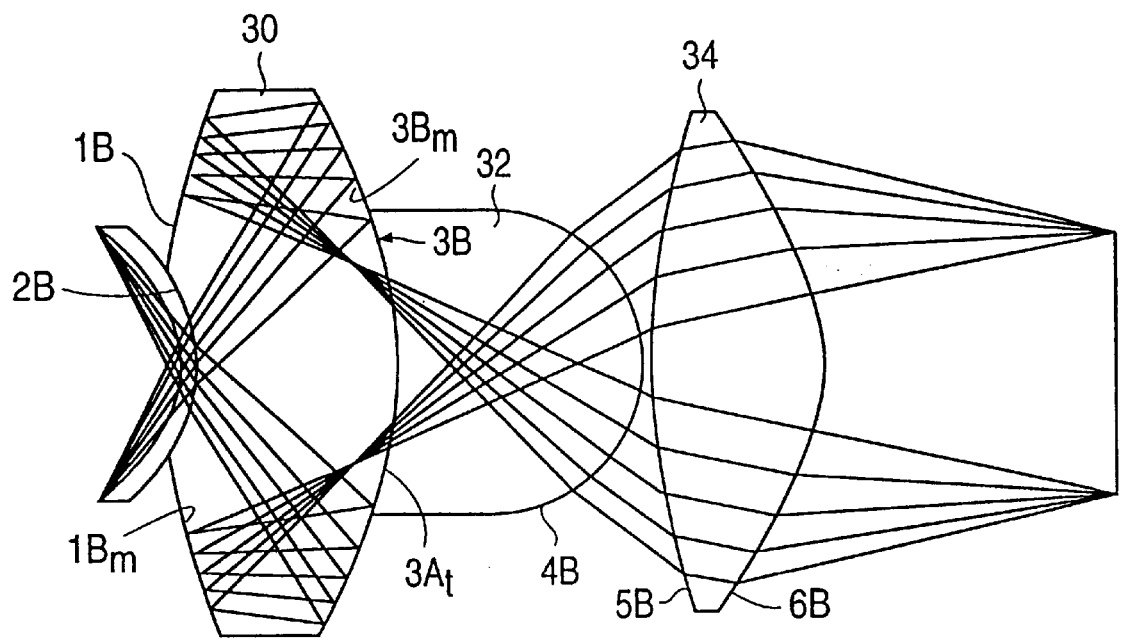

FIG. 3 illustrates a gonioscopic viewing system, including a lens component 30, lens cap 32 and biconvex lens 34, which is similar to the embodiment of FIG. 2 in that a double aspheric, double reflecting mirror system is utilized. However, departing from the symmetrical mirror design of FIG. 2, the system of FIG. 3 utilizes a non-symmetrical mirror arrangement with posterior and anterior reflecting surfaces having both different radii and different conic constant values. The gonioscopic viewing system of FIG. 3 provides a reduced magnification of the real aerial image while allowing a larger circumferential area of the trabecular mesh work to be seen in a single view. The surfaces in FIG. 3 have reference numerals which have the same number as corresponding surfaces in FIG. 2 followed by the suffix "B" rather than "A." A similar convention is used below in describing other embodiments of the invention, with corresponding surfaces having the same reference numeral followed by a different letter of the alphabet to distinguish the embodiments from one another.

Surface data of an exemplary construction of the embodiment of FIG. 3 is contained in Table 3 below, wherein the lens component 30 and lens cap 32 are both made of PMMA acrylic and biconvex lens 34 is made of LAH 58 glass. A gonioscopic viewing system constructed in accordance with the exemplary surface data in Table 3 and the materials mentioned above produces a real, aerial image spaced 13.7 mm anterior of convex surface 6B when placed on an eye.

TABLE 3

(FIG. 3)

| Surface No. | Apical Radius (r) | Conic Constant (k) | Diameter (mm) | Spacing from Apex of Posterior Contact Surface (mm) |
|---|---|---|---|---|
| 1B | 25.0 | −5.599295 | 24.0 | −1.5 |
| 2B | −8.0 | 0 | 9.2 | 0 |
| 3B | −20.5 | −0.1047366 | 24.0 | 9.0 |
| 4B | −6.5 | −0.08637812 | 13.4 | 21.05 |
| 5B | 31.06588 | −4.567719 | 22.0 | 21.55 |
| 6B | −11.29668 | −2.283859 | 22.0 | 28.55 |

Figure 4:
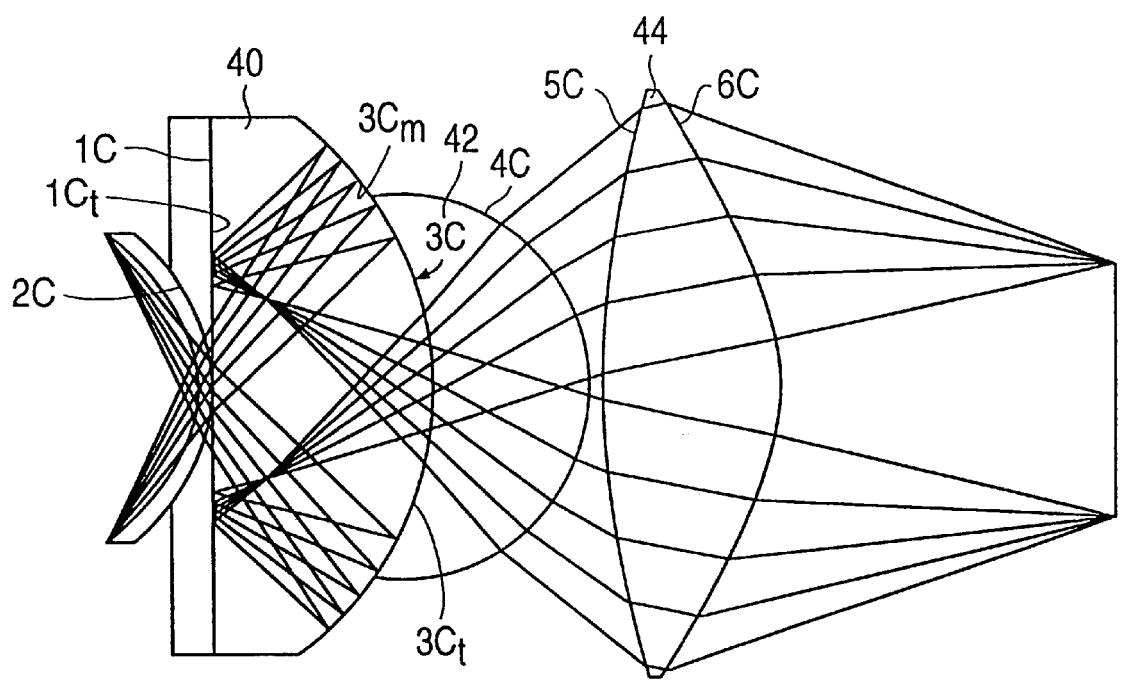

FIG. 4 shows an embodiment of a gonioscopic viewing system which is similar to that of FIGS. 2 and 3 except that the posterior mirror surface 1C$_t$ is flat. In FIG. 4, the reference numerals denoting the surfaces correspond to the reference numerals in prior figures but have the suffix "C". The gonioscopic viewing system of FIG. 4 allows further reduced image size on the order of 1.0 magnification. In this embodiment, the anterior mirror surface comprises an oblate ellipsoid with a conic constant value of 0.03525. Although an aspheric mirror surface has been utilized, it is within the scope of the invention that either a non-aspheric or spherical mirror surface may be employed.

Surface data of an exemplary configuration of the embodiment according to FIG. 4 is provided below in Table 4 wherein lens component 40 and lens cap 42 are made of PMMA acrylic and biconvex lens 44 is made of LAH-58 glass. A gonioscopic viewing system made in accordance with the exemplary configuration of the embodiment of FIG. 4 will result in a real image produced at 13.7 mm anterior of surface 6C.

TABLE 4

(FIG. 4)

| Surface No. | Apical Radius (r) | Conic Constant (k) | Diameter (mm) | Spacing from Apex of Posterior Contact Surface (mm) |
|---|---|---|---|---|
| 1C | ∞ | — | — | 0 |
| 2C | −8.0 | 0 | 9.2 | 0 |
| 3C | −12.5 | −0.0352028 | 21.0 | 9.0 |
| 4C | −6.5 | −0.2570157 | 15.0 | 16.0 |
| 5C | 31.57481 | −4.243685 | 23.0 | 16.5 |
| 6C | −11.48175 | −2.121843 | 23.0 | 23.5 |

Figure 5:
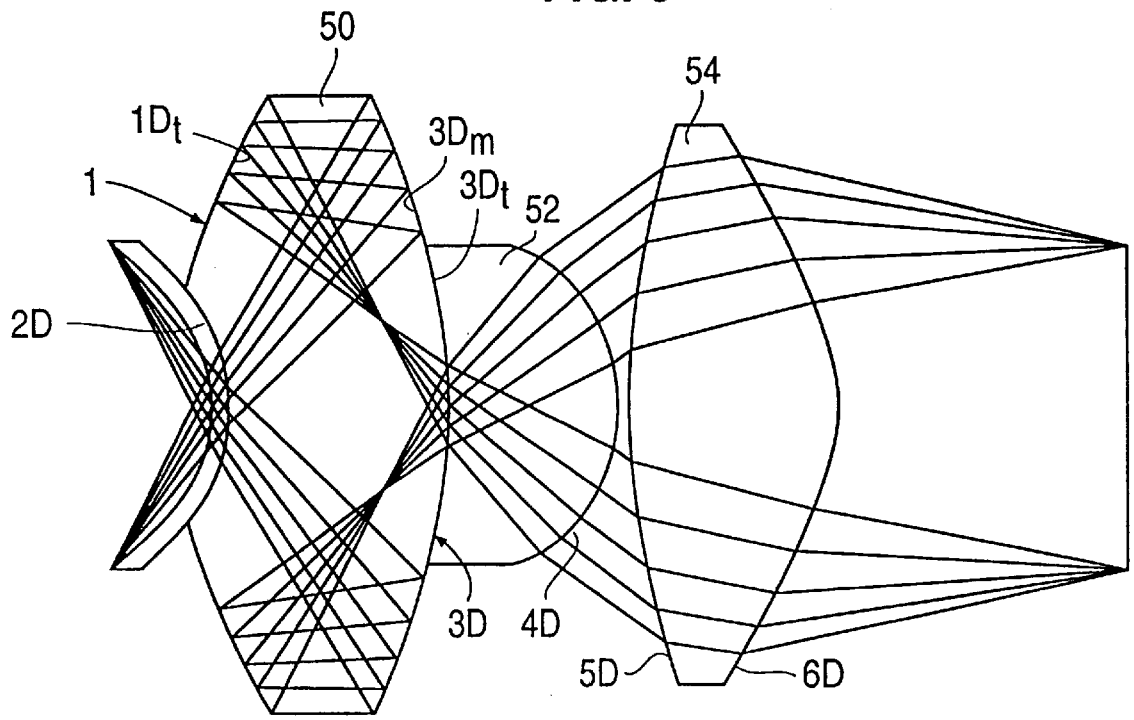

FIG. 5 shows an embodiment of a gonioscopic viewing system which is similar to that illustrated in FIG. 2 but which includes a lens cap 52 comprised of LAH-58 glass rather than PMMA acrylic in order to provide significantly greater light ray bending as the light rays proceed through the system. Although the use of the more expensive LAH-58 glass may increase cost of the system, the optical quality achieved by utilizing a more nearly symmetrical mirror system may be advantageous as the angle of the chief rays proceeding toward the conjugate pupil location is steeper than the angle of the corresponding chief rays as seen in the embodiments shown in FIGS. 3 and 4. The LAH-58 glass has been selected in order to provide greater ray conversions and ultimately a reduced image magnification. The reference numerals denoting the surfaces in FIG. 5 correspond to the reference numerals in prior Figures but have the suffix "D."

Surface data of an exemplary configuration of the embodiment according to FIG. 5 is provided below in Table 5 wherein lens component 50 is made of PMMA acrylic and biconvex lens 54 is made of the same LAH-58 glass as lens cap 52. The gonioscopic viewing system made in accordance with the exemplary configuration of FIG. 5 will result in a real image produced at 11.5 mm anterior of surface 6D.

TABLE 5

(FIG. 5)

| Surface No. | Apical Radius (r) | Conic Constant (k) | Diameter (mm) | Spacing from Apex of Posterior Contact Surface (mm) |
|---|---|---|---|---|
| 1D | 20.5 | −1.0 | 24.0 | −2.0 |
| 2D | −8.0 | 0 | 9.2 | 0 |
| 3D | −20.5 | −1.0 | 24.0 | 9.0 |
| 4D | −6.5 | 0 | 12.0 | 18.0 |
| 5D | 26.90302 | −6.371623 | 21.0 | 18.5 |
| 6D | −9.782915 | −3.185811 | 21.0 | 25.8 |

Figure 6:
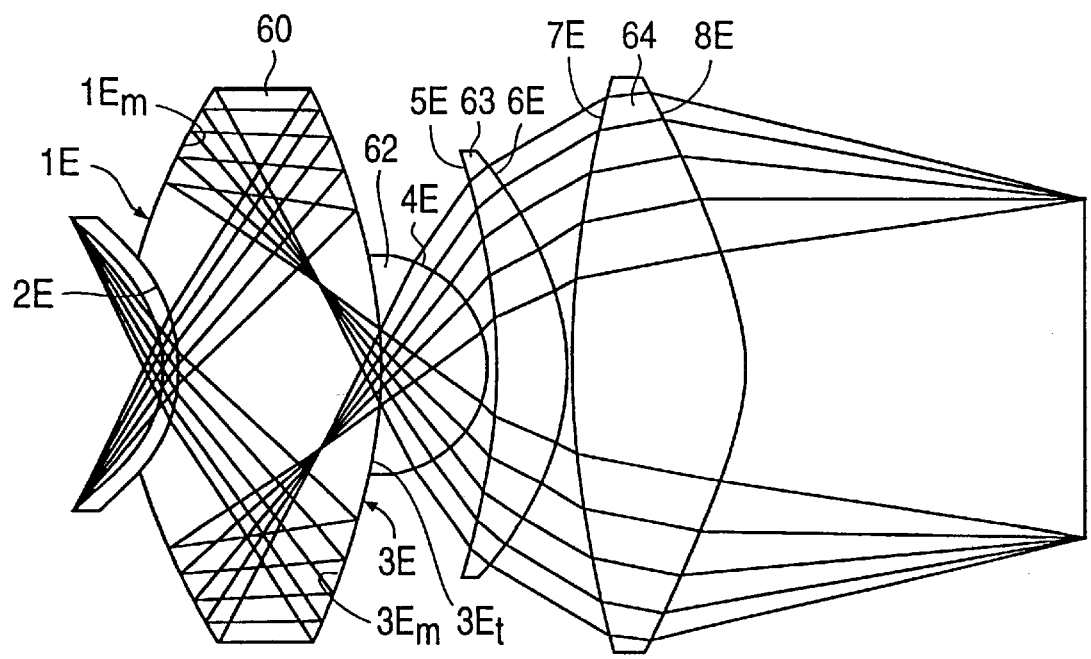

FIG. 6 illustrates a further embodiment of a gonioscopic viewing system according to the invention which utilizes a lens component 60 having a symmetrical mirror system like that of the embodiment shown in FIG. 2 and additionally includes a middle lens element 63 disposed between lens cap 62 and biconvex lens 64 to achieve additional light bending in conjunction with the other lenses. Lens element 63 is shown as being in the shape of a meniscus lens having a concave posterior surface 5E and a convex anterior surface 6E. Biconvex lens 64 has opposed posterior and anterior convex surfaces 7E and 8E, respectively. Otherwise, surfaces 1E, 2E, 3E and 4E correspond respectively to the surfaces 1A, 2A, 3A and 4A in FIG. 2.

Surface data of an exemplary configuration of the embodiment according to FIG. 6 is provided below in Table 6 wherein lens component 60 and lens cap 62 are made of PMMA acrylic, middle lens element 63 is made of LAL-59 glass which has an index of refraction of 1.734, and biconvex lens 64 is made of LAH-58 glass.

A gonioscopic viewing system made in accordance with the exemplary configuration of the embodiment of FIG. 6 will result in a real image produced at 15.00 mm anterior of surface 8E.

TABLE 6

(FIG. 6)

| Surface No. | Apical Radius (r) | Conic Constant (k) | Diameter (mm) | Spacing from Apex of Posterior Contact Surface (mm) |
|---|---|---|---|---|
| 1E | 20.5 | −1.0 | 24.0 | −2.0 |
| 2E | −8.0 | 0 | 9.2 | 0 |
| 3E | −20.5 | −1.0 | 24.0 | 9.0 |
| 4E | −4.5 | 0 | 14.0 | 14.0 |
| 5E | −23.09917 | 0 | 17.0 | 14.5 |
| 6E | −12.00702 | 0 | 18.0 | 17.5 |
| 7E | 42.83011 | −5.248419 | 24.0 | 18.0 |
| 8E | −15.57459 | −2.624209 | 24.0 | 24.5 |

Figure 7:
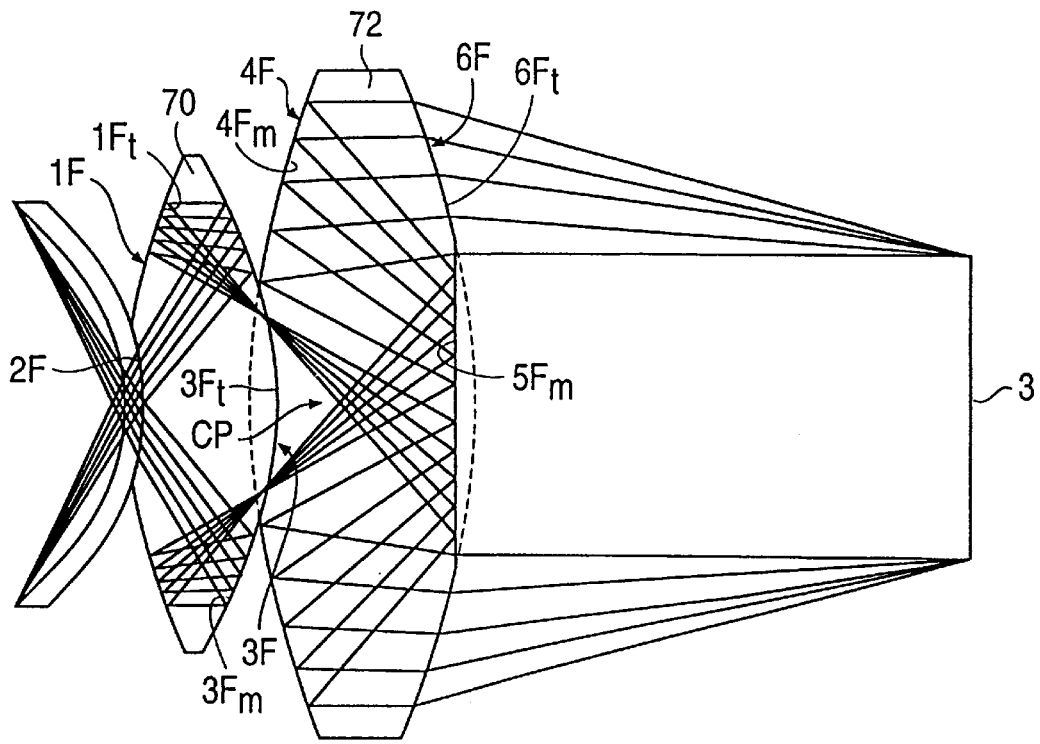

FIG. 7 illustrates an embodiment of the invention which departs from the embodiments illustrated in FIGS. 2–6 by utilizing four reflecting surfaces instead of two reflecting surfaces to achieve an upright and correctly oriented aerial image of the angle. In this embodiment, two double aspheric biconvex lens components 70 and 72, which provide the basic form of the reflecting system, have been optically cemented together where the surface curvature of the central area of at least one element has been shaped so that it may be easily cemented to the other. In the depicted example illustrated in FIG. 7, convex posterior surface 4F of biconvex lens component 72 has been shaped in its middle region to have a surface curvature matching the convex curvature of anterior surface 3F of lens component 70. Lens component 72 has a convex anterior surface 6F which has a flat central region provided with a reflective coating to form a flat mirror surface $5F_m$. Thus, convex anterior surface 6F is transmissive only in a peripheral region $6F_t$. The imaginary continuation of convex surface 6F in a middle region of lens component 72 is indicated by a dashed line. Lens component 70 is shaped similarly to the asymmetric lens component 30 in FIG. 3 and is thus provided with opposing convex surfaces 1F and 3F which are provided with reflective coatings in peripheral regions to result in mirror surfaces $1F_m$ and $3F_m$, respectively. A middle region $3F_t$ of surface 3F is uncoated and therefore transmits light. A middle region of posterior surface 1F is shaped to provide a concave posterior contact surface 2F which has a curvature corresponding to the average cornea similar to the concave posterior contacting surfaces in prior embodiments. As shown by the overlaid ray tracing in FIG. 7, light emanating from the anterior chamber angle enters lens component 70 at the concave posterior surface 2F and is reflected and focussed by concave anterior mirror surface $3F_m$ toward concave posterior mirror surface $1F_t$ which reflects and focusses the light to form a real intermediate image within the system which is reversed and inverted. The light subsequently proceeds toward a conjugate pupil area CP where the principal rays cross one another as well as the optical axis and reflected off flat mirror surface $5F_m$ posteriorly toward concave mirror surface $4F_m$ where the light is reflected in anterior direction through convex anterior surface $6F_t$ where the light is refracted and focussed toward an image plane I to produce a true, upright real aerial image of the anterior chamber angle of the eye.

In an exemplary construction of the embodiment illustrated in FIG. 7, lens component 70 and 72 are both made of PMMA acrylic and exemplary surface data is shown in Table 7 below. A gonioscopic viewing system constructed in accordance with the exemplary configuration will result in an image produced at 15 mm anterior of surface 6F of lens component 72.

TABLE 7

(FIG. 7)

| Surface No. | Apical Radius (r) | Conic Constant (k) | Diameter (mm) | Spacing from Apex of Posterior Contact Surface (mm) |
|---|---|---|---|---|
| 1F | 15.0 | −1.0 | 15.0 | −0.5 |
| 2F | −8.0 | 0 | 4.0 | 0 |
| 3F | −11.0 | −1.0 | 15.0 | 4.5 |
| 4F | 20.2003 | −1.382884 | 20.0 | 3.6 |
| 5F | ∞ | — | 4 | 10.6 |
| 6F | −20.2003 | −1.382884 | 20.0 | 11.1 |

Figure 8:
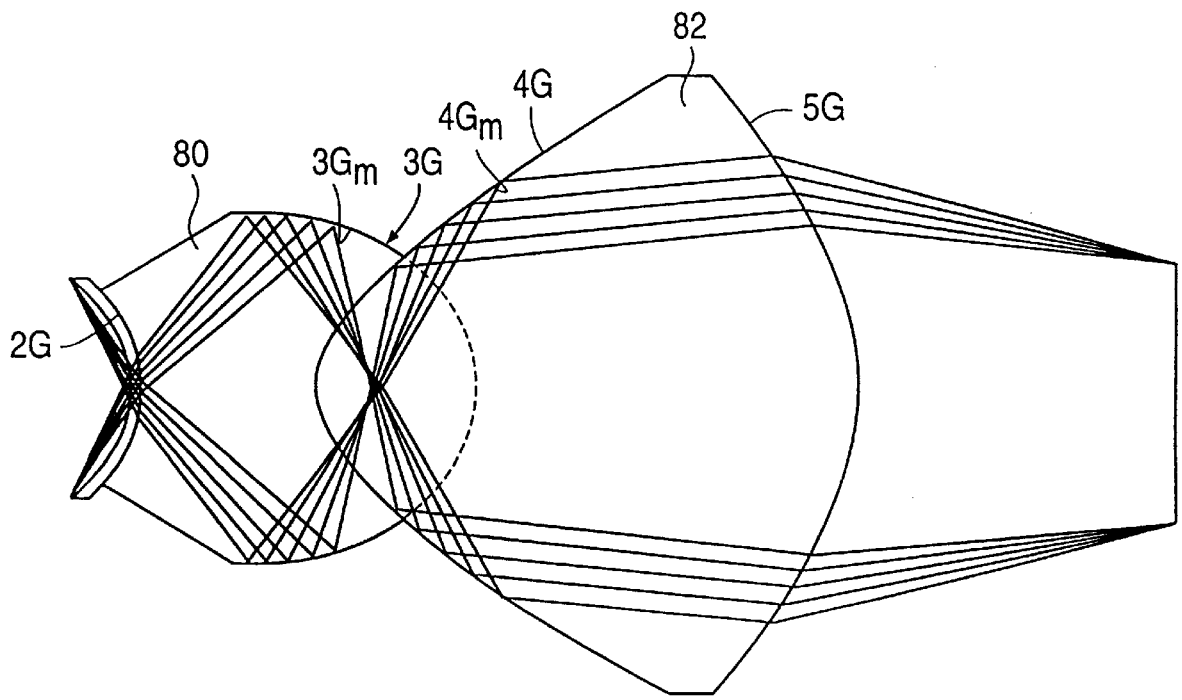

FIG. 8 illustrates a modified embodiment of a gonioscopic viewing system for producing a real aerial image of the angle. In this embodiment, a solid PMMA acrylic component 80 has a concave posterior surface with a shape substantially corresponding to the average cornea and an ellipsoidal anterior surface 3G which is provided with a reflective coating to form an ellipsoidal mirror surface $3G_m$. The ellipsoidal shape of mirror surface $3G_m$ is such that when concave posterior surface 2G is in place on an eye, a first focus of ellipsoidal mirror surface $3G_m$ is coincident with the exit pupil of the eye so that light rays emanating from the angle enter lens component 80 and are reflected off ellipsoidal mirror surface $3G_m$ toward a second focus of the ellipsoidal mirror surface, crossing the optical axis toward a second and final aspheric mirror formed by a reflectively coated parabolic surface 4G of a PMMA acrylic component 82. Parabolic surface 4G has a central region that is uncoated and which is glued to lens component 80 which has a corresponding central region removed and shaped to match the parabolic shape of surface 4G of lens component 82. Lens component 82 is further provided with a convex anterior surface 5G which refracts and focusses light reflected from parabolic mirror surface $4G_m$ for forming an aerial real image of the anterior chamber angle anterior of the viewing system. Table 8 below provides surface data of an exemplary configuration of the embodiment of FIG. 8 wherein convex anterior surface 5G is additionally provided with a sixth order deformation term having a coefficient of $2.571003e^{-008}$ in accordance with the formula for aspheric surface set forth here and above.

A gonioscopic viewing system made in accordance with the exemplary data mentioned above will produce a real aerial image in a plane 18.1 mm anterior of surface 5G.

TABLE 8

(FIG. 8)

| Surface No. | Apical Radius (r) | Conic Constant (k) | Diameter (mm) | Spacing from Apex of Posterior Contact Surface (mm) |
|---|---|---|---|---|
| 2G | −8.0 | 0 | 9.0 | 0 |
| 3G | −8.0 | −0.33 | 19.5 | 16.5 |
| 4G | 5.8 | −1.1 | 34.0 | 7.75 |
| 5G | −19.86896 | −0.5 | 34.0 | 38.75 |

Figure 9:
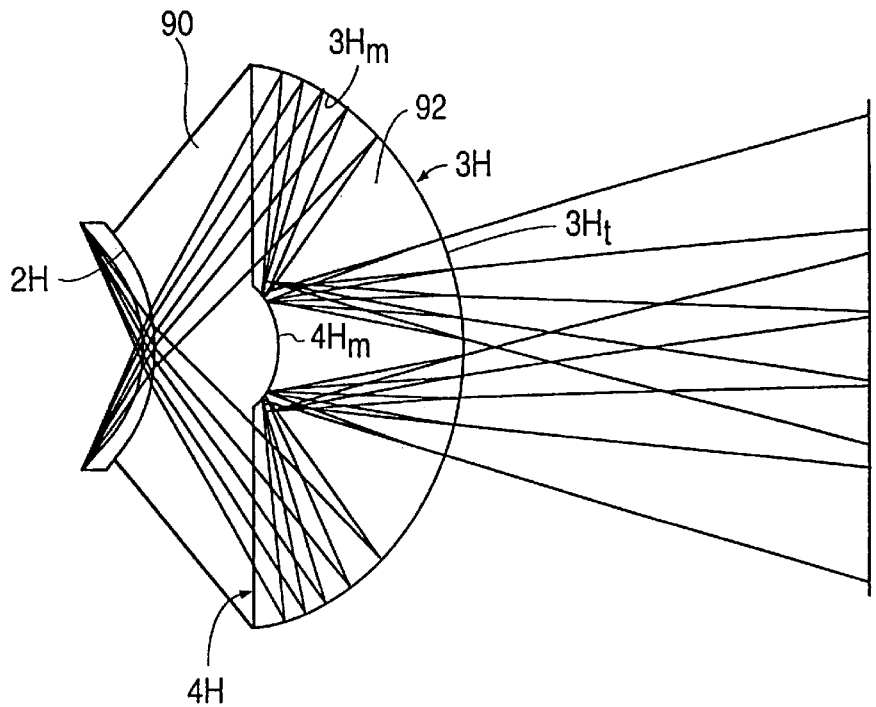

FIG. 9 illustrates a further embodiment of the invention employing a double mirror system wherein the posterior mirror surface is convex as opposed to being concave as in the embodiments shown in FIGS. 2–6. As shown in FIG. 9, a first lens component 90 includes the concave posterior contact lens surface 2H and has a posterior surface which is shaped for being glued to a matching posterior surface 4H of an anterior lens component 92. Anterior lens component 92 has a posterior surface 4H that has a central concave region that is provided reflective coating to form a convex mirror surface $4H_m$. Posterior surface 4H is uncoated in the region peripheral to the convex mirror surface $4H_m$. Anterior lens portion 92 has a convex anterior surface 3H which is provided with a reflective coating in a peripheral region to form a concave mirror surface $3H_m$ and is uncoated in a central region so as to provide a central refracting surface $3H_r$.

In the embodiment of FIG. 9, light from the anterior chamber angle enters the viewing system through concave posterior surface 2H and is reflected off concave anterior surface $3H_m$ in a posterior direction where the light is reflected off the central convex posterior mirror surface $4H_m$ and focussed thereby to form a real image within lens portion 92. This embodiment does not provide an upright and correctly oriented image but may be preferable in that the image that can be viewed is significantly reduced in magnification with respect to the size and extent of the actual structure of the angle, thus allowing the entire annular shaped image of the anterior chamber angle to be seen in a single view.

Figure 10:
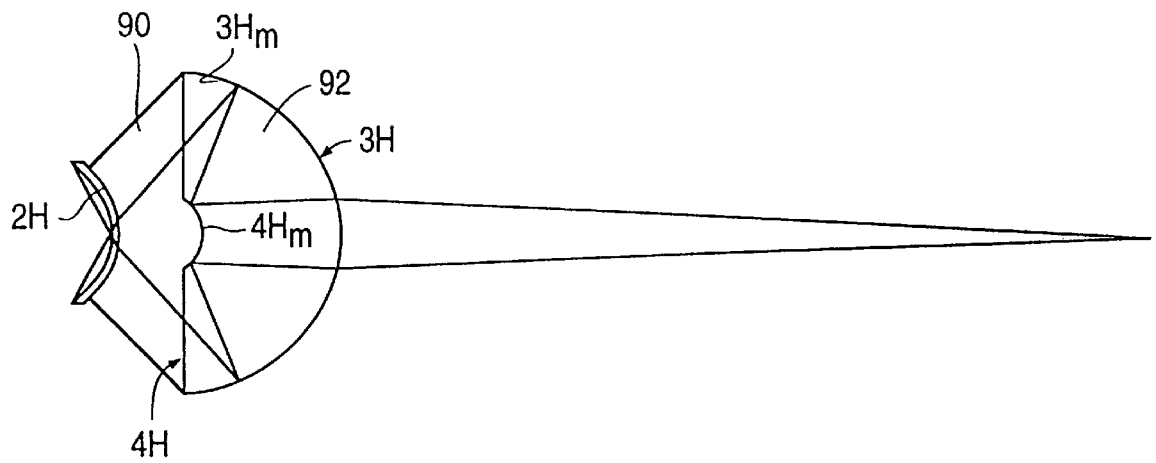
FIG. 10 shows the embodiment of a gonioscopic viewing system according to FIG. 9, with only the path of the principal rays being shown.

FIG. 10 shows more clearly the direction of the chief rays through the embodiment of the gonioscopic viewing system illustrated in FIG. 9. As shown in FIG. 10, the chief rays exiting the system and proceeding to a slip lamp objective lens correctly proceed generally toward a conjugate pupil location coincident with that of the slit lamp biomicroscope.

TABLE 9

(FIG. 9)

| Surface No. | Apical Radius (r) | Conic Constant (k) | Diameter (mm) | Spacing from Apex of Posterior Contact Surface (mm) |
|---|---|---|---|---|
| 2H | −8.0 | 0 | 12.0 | 0 |
| 3H | −14.0 | −0.0672045 | 28.0 | 17.0 |
| 4H | −3.5 | −0.6640848 | 7.0 | 6.75 |

As mentioned previously, I have discovered that the surface characteristics of the mirrored gonioscopic viewing systems described above can be modified so that the systems perform an indirect ophthalmoscopy application for viewing the fundus. Thus, FIGS. 11–18 correspond to the embodiments illustrated in FIGS. 2, 3, 5, 6, 7, 8 and 9, respectively, so that the same reference numerals have been used in FIGS. 11–18 as used in the respective embodiments of the gonioscopic viewing system. The only difference is that in FIGS. 11–18, because the surface characteristics, i.e., radius of curvature, conic constants and in some cases spacing of the lenses and index of refraction have been modified, when the system is placed on an eye the fundus will be imaged rather than the anterior chamber angle. In FIGS. 11–18, as well as FIG. 19, which is a modified version of the embodiment of FIG. 18, the ray tracings are with respect to light emanating from different points on the fundus of a patient's eye which is not shown. Although the ray tracings show proceeding as parallel bundles from an entrance pupil in air, the ray tracings through the lens systems follow the same pathways as do light rays which originate at the retina and proceed through the vitreous humor, crystalline lens, and aqueous humor and cornea of the eye to the various lens elements of the illustrated embodiments. The use of parallel bundles in air is a simplified representation of the optical system of the emotropic human eye. In FIGS. 11, 12 and 14–18, only the surfaces are designated by reference numerals which are identical with the corresponding embodiments of the gonioscopic viewing system of FIGS. 2, 3 and 5–9, respectively. Tables 10–16 provide surface data of exemplary configurations of the embodiments of the indirect ophthalmoscopy viewing systems illustrated by FIGS. 11–18 which will result in a real image of the fundus created outside of the eye. As with the above described gonioscopic viewing systems, the indirect ophthalmoscopy systems of FIGS. 11–17 will produce a true, upright aerial image of the fundus anterior of the viewing system whereas the embodiment illustrated in FIG. 18 will produce an inverted, reversed image of the fundus within the viewing system.

Figure 11:
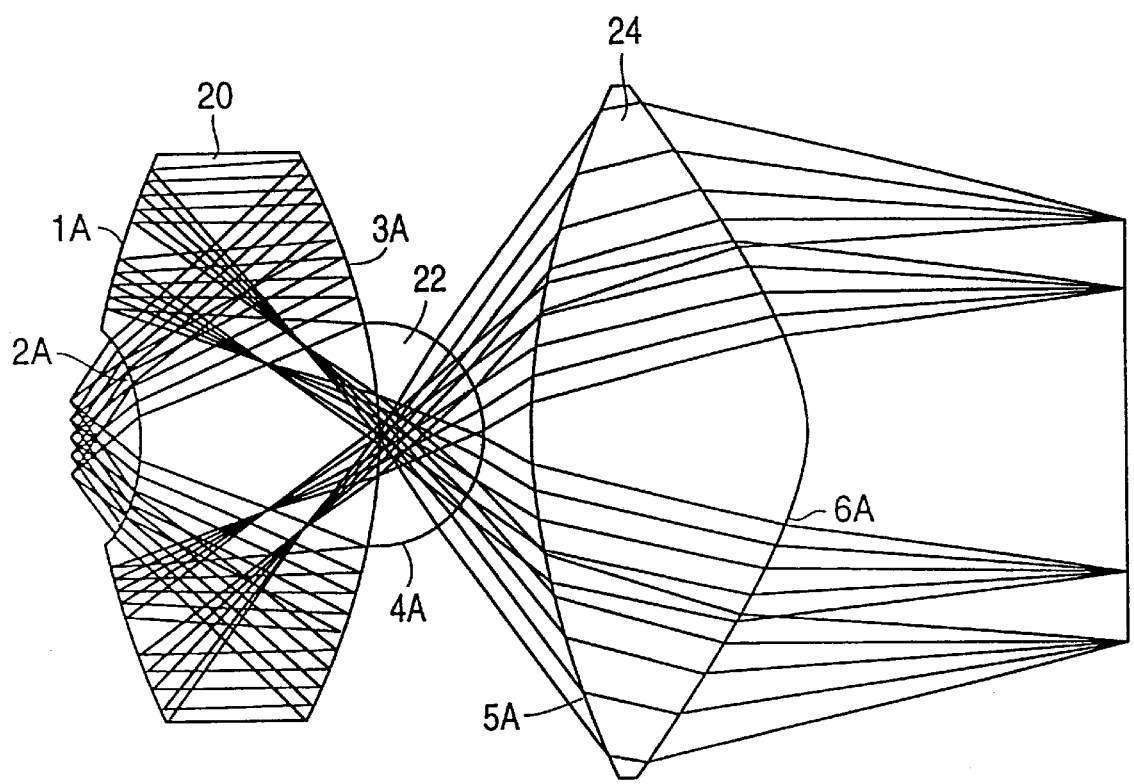
FIGS. 11 through 19 are schematic side sectional views of indirect ophthalmoscopy lens systems incorporating mirrored surfaces for viewing a real image of the eye fundus according to further aspects of the invention.

In the exemplary construction of FIG. 11 embodiments, lens component 20 and lens cap 22 comprise PMMA acrylic and biconvex lens 24 is LAL-59 glass having an index of refraction of 1.734.

TABLE 10

(FIG. 11)

| Surface No. | Apical Radius (r) | Conic Constant (k) | Diameter (mm) | Spacing from Apex of Posterior Contact Surface (mm) |
|---|---|---|---|---|
| 1A | −24.5 | −1.0 | 24.0 | −2.0 |
| 2A | −7.55 | −0.18 | 9.2 | 0 |
| 3A | −24.5 | −1.0 | 24.0 | 9.0 |
| 4A | −4.5 | 0 | 14.0 | 14.0 |
| 5A | 20.05 | −4.280707 | 29.0 | 16.0 |
| 6A | −10.025 | −2.140353 | 29.0 | 28.0 |

Figure 12:
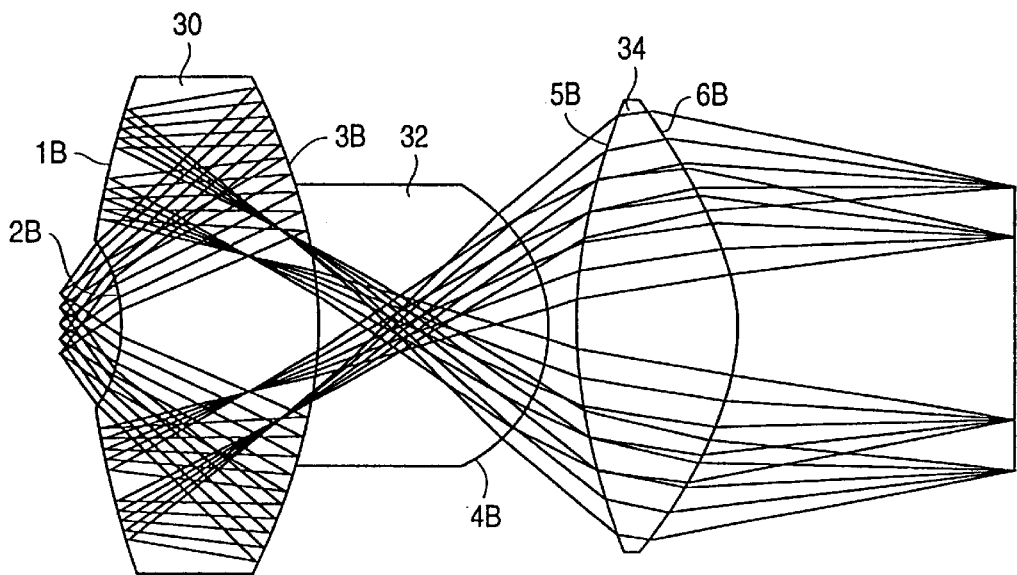
Figure 13:
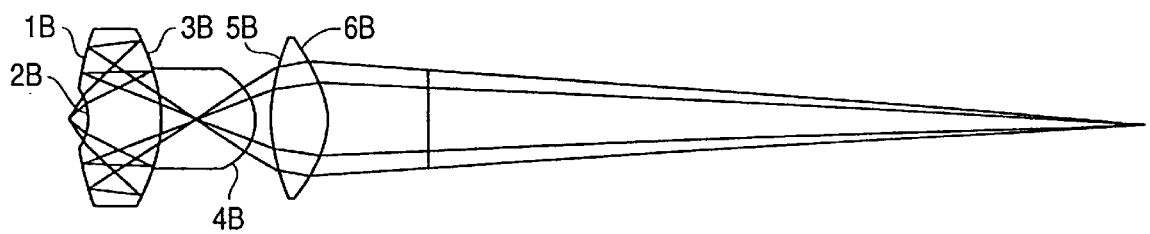

FIG. 13 illustrates the embodiment of FIG. 12 with only the chief rays being illustrated to show that the chief rays exiting the system proceed generally toward a conjugate pupil location at which a slit lamp objective lens can be located for viewing the real aerial image. In the exemplary construction of the embodiments of FIGS. 12 and 13, the lens component 30 and lens cap 32 each comprise PMMA acrylic and biconvex lens 34 is LAL-59 glass.

TABLE 11

(FIG. 12)

| Surface No. | Apical Radius (r) | Conic Constant (k) | Diameter (mm) | Spacing from Apex of Posterior Contact Surface (mm) |
|---|---|---|---|---|
| 1B | 29.87805 | −5.599295 | 24.0 | −1.5 |
| 2B | −7.55 | −0.18 | 9.2 | 0 |
| 3B | −24.5 | −0.1047366 | 24.0 | 9.0 |
| 4B | −6.5 | −0.303068 | 13.4 | 21.05 |
| 5B | 23.2 | −3.752854 | 22.0 | 22.55 |
| 6B | −11.6 | −1.876427 | 22.0 | 30.05 |

Figure 14:
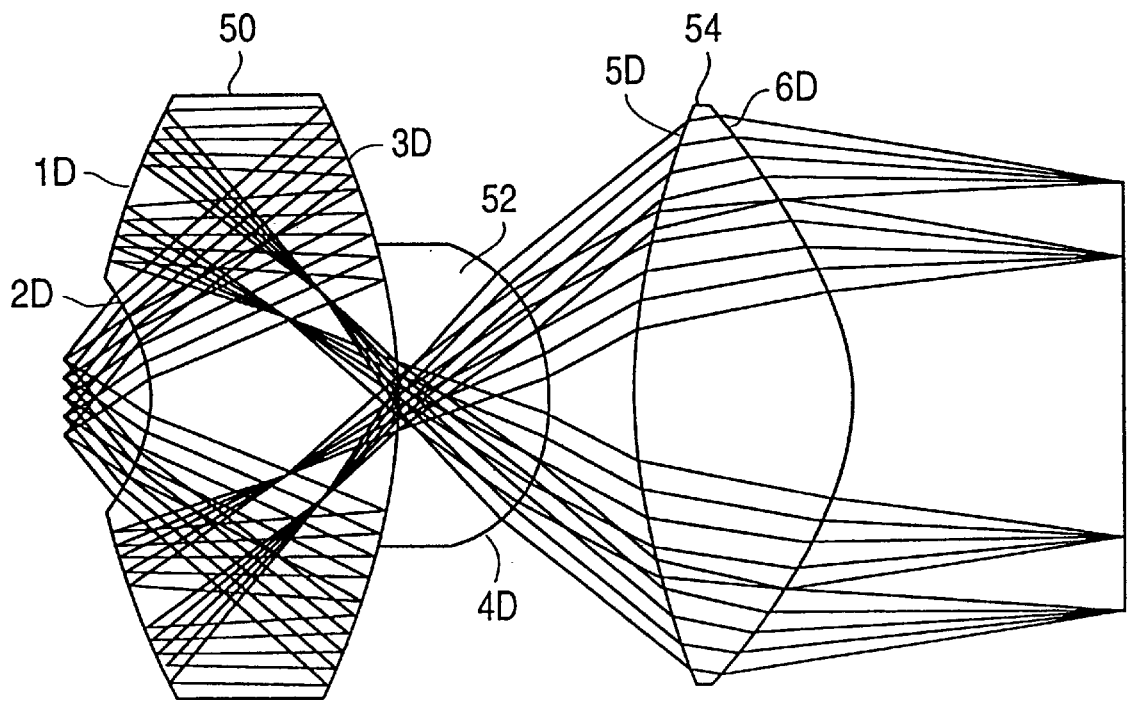

In the following exemplary construction of the FIG. 14 embodiment, lens component 50 is PMMA acrylic, lens cap 52 is LAH-58 glass and biconvex lens 54 is LAL-59 glass. Additionally surface 6D has a sixth order deformation coefficient of $1.669521e^{-008}$.

TABLE 12

(FIG. 14)

| Surface No. | Apical Radius (r) | Conic Constant (k) | Diameter (mm) | Spacing from Apex of Posterior Contact Surface (mm) |
|---|---|---|---|---|
| 1D | 24.5 | −1.0 | 24.0 | −2.0 |
| 2D | −7.55 | −0.18 | 9.2 | 0 |
| 3D | −24.5 | −1.0 | 24.0 | 9.0 |
| 4D | −6.5 | 0 | 13.0 | 18.0 |
| 5D | 23.27892 | −4.459783 | 23.0 | 22.0 |
| 6D | −11.63946 | −2.229892 | 23.0 | 29.5 |

Figure 15:
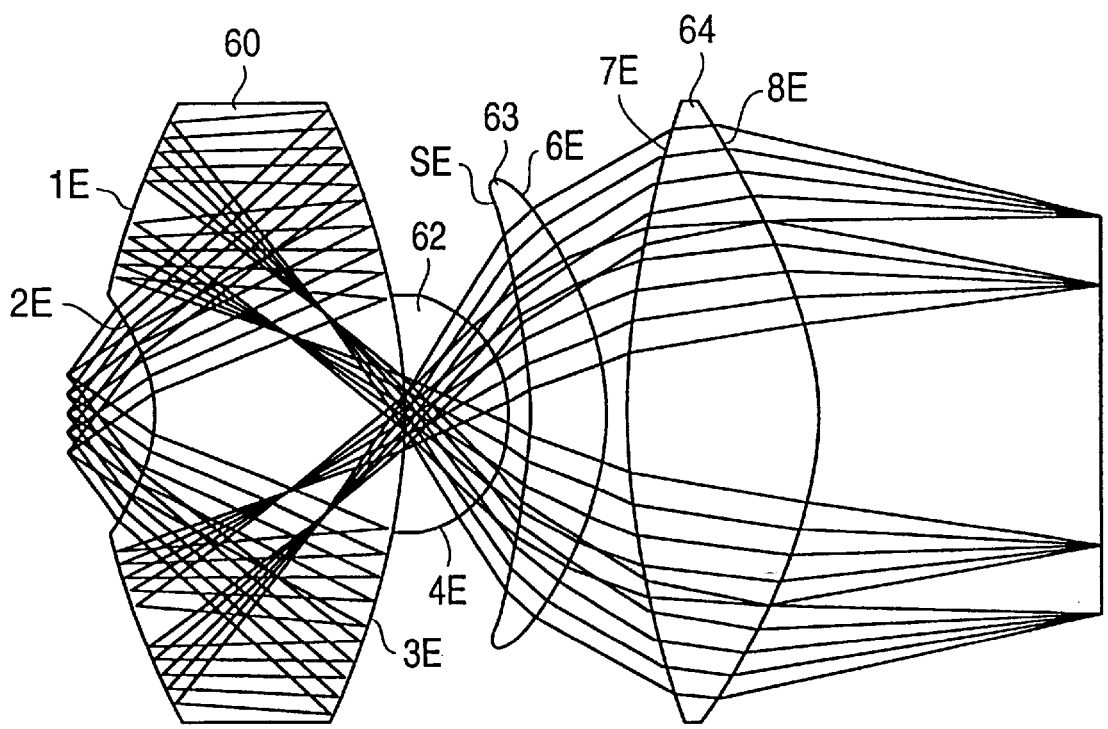

In the following exemplary construction of the FIG. 15 embodiment, lens component 60 and lens cap 62 are PMMA acrylic, intermediate meniscus lens 63 is LAH-55 glass (index of refraction=1.835) and biconvex lens 64 is LAL-59 glass. Additionally, surface 8E has a sixth order deformation coefficient of $3.25112e^{-007}$.

TABLE 13

(FIG. 15)

| Surface No. | Apical Radius (r) | Conic Constant (k) | Diameter (mm) | Spacing from Apex of Posterior Contact Surface (mm) |
|---|---|---|---|---|
| 1E | 24.5 | −1.0 | 24.0 | −2.0 |
| 2E | −7.55 | −0.18 | 9.2 | 0 |
| 3E | −24.5 | −1.0 | 24.0 | 9.0 |
| 4E | −4.5 | 0 | 14 | 14.0 |
| 5E | −22.0 | 0 | 17.0 | 15.0 |
| 6E | −11.0 | o | 18.0 | 18.5 |
| 7E | 34.53901 | 0.1697051 | 15.14954 | 19.5 |
| 8E | −17.2695 | 0.08485255 | 15.14954 | 26.15 |

Figure 16:
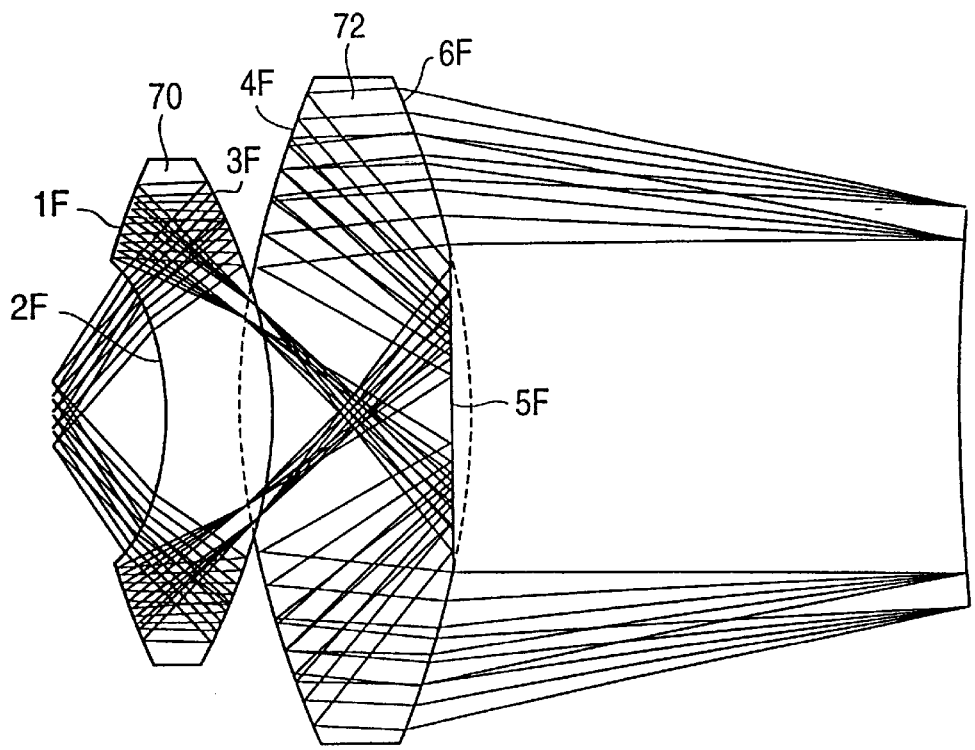
Figure 17:
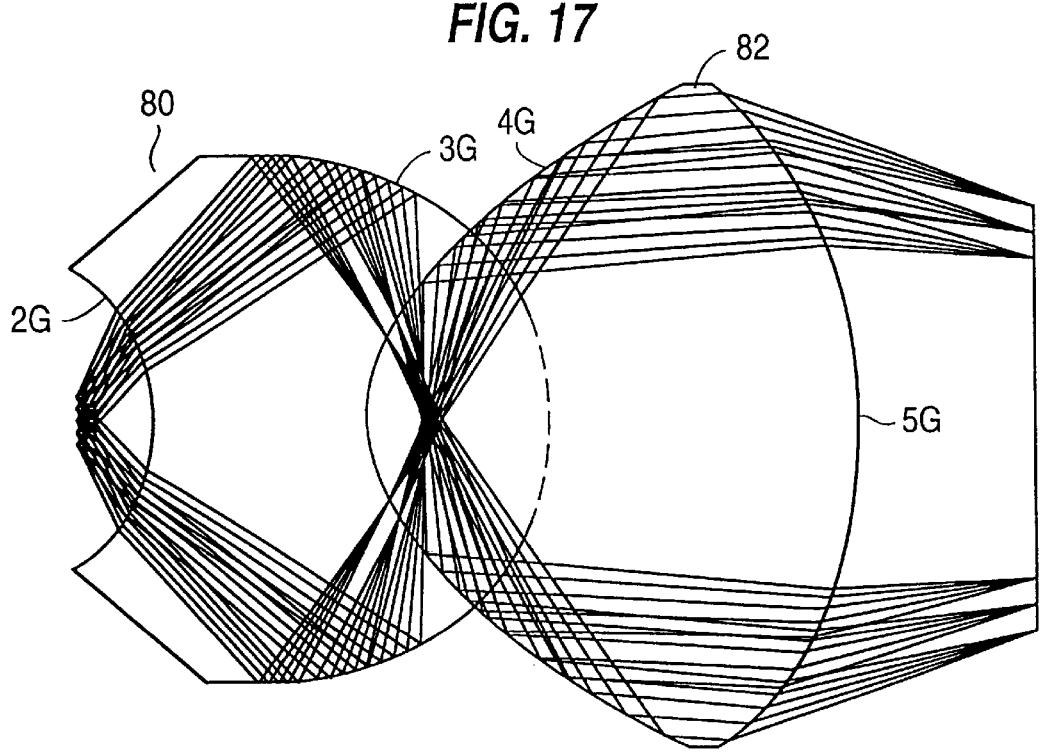
Figure 18:
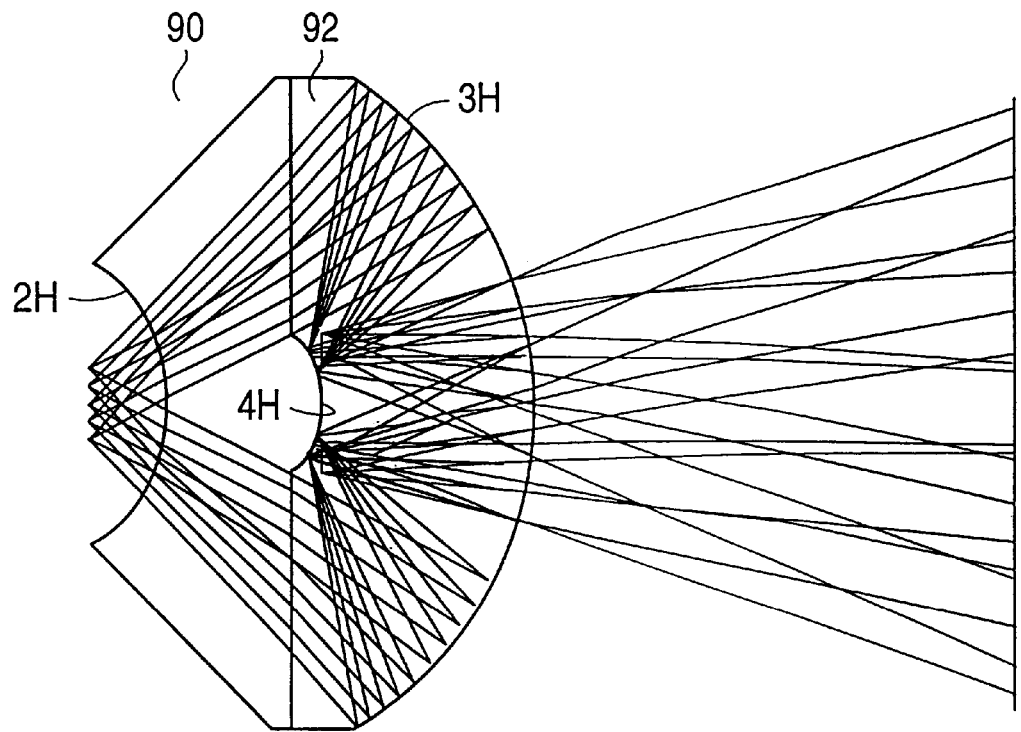

In the exemplary construction of the FIG. 16 embodiment, lens components 70 and 72 are both PMMA acrylic as are components 80, 82 and 90, 92 in the exemplary construction of the FIG. 17 and FIG. 18 embodiments. Additionally, surface 5G in FIG. 17 has a fourth order deformation coefficient of −0.0001000297 and a sixth order deformation coefficient of $2.2e^{-007}$.

TABLE 14

(FIG. 16)

| Surface No. | Apical Radius (r) | Conic Constant (k) | Diameter (mm) | Spacing from Apex of Posterior Contact Surface (mm) |
|---|---|---|---|---|
| 1F | 17.5 | −1.0 | 15.0 | −2.0 |
| 2F | −7.55 | −0.18 | 12.4 | 0 |
| 3F | −12.8333 | −1.0 | 15.0 | 3.0 |
| 4F | 21.5 | −1.16 | 20.0 | 2.1 |
| 5F | ∞ | — | 20.0 | 9.1 |
| 6F | −21.5 | −1.16 | 20.0 | 9.6 |

TABLE 15

(FIG. 17)

| Surface No. | Apical Radius (r) | Conic Constant (k) | Diameter (mm) | Spacing from Apex of Posterior Contact Surface (mm) |
|---|---|---|---|---|
| 2G | −7.55 | −0.18 | 12.4 | 0 |
| 3G | −9.0 | −0.33 | 21.9 | 17.0 |
| 4G | 5.8 | −1.1 | 28.0 | 8.25 |
| 5G | −35.0 | 0 | 28.0 | 29.25 |

TABLE 16

(FIG. 18)

| Surface No. | Apical Radius (r) | Conic Constant (k) | Diameter (mm) | Spacing from Apex of Posterior Contact Surface (mm) |
|---|---|---|---|---|
| 2H | −7.55 | −0.18 | 12.0 | 0 |
| 3H | −15.27 | −0.067204 | 28.0 | 17.0 |
| 4H | −3.5 | −0.6640848 | 6.0 | 6.75 |

Figure 19:
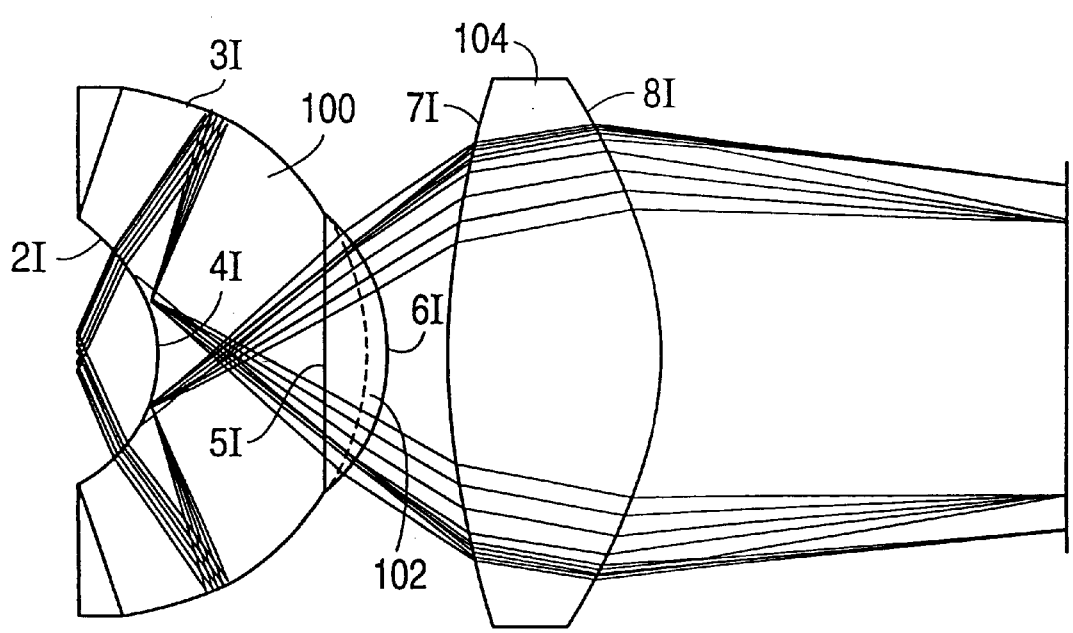

The embodiment illustrated in FIG. 19 is a modified version of the embodiment shown in FIG. 18. In the embodiment of FIG. 19, the convex mirror surface is located adjacent the corneal contacting surface itself. Additionally, lens component 100 has a planar anterior surface to which is optically glued a lens cap 102 to provide further bending of the light rays toward the biconvex lens 104 which is utilized to produce a true, upright real aerial image of the fundus which is initially imaged as an intermediate image that is upside down and reversed within lens 100 as previously described in connection with the embodiment of FIG. 18 as well as the corresponding embodiment of FIG. 9. Table 17 below provides exemplary data for the correspondingly numbered surfaces in FIG. 19 for an exemplary configuration of this embodiment wherein lens component 100 is PMMA acrylic, lens cap 102 is LAL-55 glass and biconvex lens 104 is LAL-59 glass. Additionally, surface 8I has a sixth order deformation coefficient of $3.933565e^{-008}$.

TABLE 17

(FIG. 19)

| Surface No. | Apical Radius (r) | Conic Constant (k) | Diameter (mm) | Spacing from Apex of Posterior Contact Surface (mm) |
|---|---|---|---|---|
| 2I | −7.55 | −0.18 | 12.0 | 0 |
| 3I | 11.7 | −0.02 | 23.1 | 9.0 |
| 4I | −7.55 | −0.18 | 12.0 | 0 |
| 5I | ∞ | — | 13.0 | 7.0 |
| 6I | −8.3 | 0 | 13.0 | 10.2 |
| 7I | 25.4106 | −5.3732 | 24.0 | 13.2 |
| 8I | −12.7053 | −2.6866 | 24.0 | 23.2 |

It will be apparent to a person of ordinary skill in the art that by further modifying the surface characteristics in an appropriate manner, a real image of various structures within the eye can be formed. Therefore, it is possible by suitable modification of the surface characteristics to image the iris, ciliary process and other internal structures of the eye.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. A gonioscopic viewing system for diagnosis or laser treatment of the anterior chamber angle of a patient's eye, comprising:

a first lens system including a concave posterior lens surface with a shape substantially corresponding to the shape of an average cornea so that, when placed on a patient's eye, light rays originating at the anterior chamber angle and passing through the aqueous humor, pass through the cornea and the posterior lens surface of the first lens system and are directed by the first lens system toward an image forming system; and an image forming system optically aligned with the first lens system for capturing the light rays directed by the first lens system and focussing the light rays to form a real image of the anterior chamber angle outside of the patient's eye.

2. The gonioscopic viewing system according to claim 1, wherein the image forming lens system comprises a biconvex lens and the real image is formed anterior of the biconvex lens.

3. The gonioscopic viewing system according to claim 2, further including an anterior convex lens surface disposed anterior of the concave posterior lens surface for bending the light rays toward the biconvex lens.

4. The gonioscopic viewing system according to claim 3, wherein the biconvex lens is spaced in an anterior direction from the anterior convex lens surface.

5. The gonioscopic viewing system according to claim 4, further comprising an intermediate meniscus shaped lens positioned between the convex anterior lens surface and the biconvex lens for further converging the light rays toward the biconvex lens.

6. The gonioscopic viewing system according to claim 1, wherein the image forming system further includes at least first and second light reflecting surfaces, one of which is curved, arranged optically in series for reflecting and focussing the captured light rays to form the real image of the anterior chamber angle outside of the patient's eye.

7. The gonioscopic viewing system according to claim 6, wherein the real image is an intermediate real image that is inverted and reversed, and the image forming system further includes a biconvex lens located anterior of the first and second reflecting surfaces for capturing and focussing the light rays forming the intermediate real image to form an upright and true real image of the anterior chamber angle.

8. The gonioscopic viewing system according to claim 7, and further including a convex anterior lens surface following the first and second reflecting surfaces for bending the light rays toward the biconvex lens.

9. The gonioscopic viewing system according to claim 8, wherein the biconvex lens is spaced in a anterior direction from the convex anterior lens surface.

10. The gonioscopic viewing system according to claim 9, further comprising an intermediate meniscus shaped lens positioned between the convex anterior lens surface and the biconvex lens for further bending the light rays toward the biconvex lens.

11. The gonioscopic viewing system according to claim 6, wherein the one curved reflecting surface is a concave reflecting surface.

12. The gonioscopic viewing system according to claim 11, wherein the concave reflecting surface constitutes the first reflecting surface and is arranged to reflect the light rays in a posterior direction, and the second reflecting surface is disposed posterior of the concave reflecting surface for reflecting light rays from the concave reflecting surface in an anterior direction to form the intermediate real image.

13. The gonioscopic viewing system according to claim 12, wherein the second reflecting surface is planar.

14. The gonioscopic viewing system according to claim 13, wherein the second reflecting surface is concave.

15. The viewing system according to claim 13, wherein the first and second reflecting surfaces are symmetrically shaped.

16. The gonioscopic viewing system according to claim 12, wherein the biconvex lens has anterior and posterior surfaces which are partially mirrored for forming third and fourth reflecting surfaces for reflecting light from the intermediate real image to form the upright and true real image anterior of the biconvex lens.

17. The gonioscopic viewing system according to claim 16, wherein the third reflecting surface is a planar surface disposed in a central region of the anterior surface of the biconvex lens and the fourth reflecting surface is in a peripheral region of the posterior surface of the biconvex lens to form a ring defining an opening through which light forming the intermediate real image passes toward the third reflecting surface.

18. The gonioscopic viewing system according to claim 17, wherein the fourth reflecting surface is a concave reflecting surface.

19. The gonioscopic viewing system according to claim 6, wherein the curved surface comprises an ellipsoidal reflecting surface for reflecting the light passing through the posterior lens surface of the first lens system generally toward a focus of the ellipsoidal surface to form a conjugate pupil region of the patient's eye, and the other reflecting surface comprises a parabolic reflecting surface for reflecting light emanating from the conjugate pupil region to form the real image.

20. The viewing system according to claim 6, wherein the other reflecting surface comprises a central convex reflecting surface and the one curved reflecting surface comprises a concave reflecting surface having a plus optical power disposed around the central convex reflecting surface for reflecting and focussing the light rays passing through the posterior lens surface of the first lens system toward the central convex reflecting surface which in turn reflects the focussed light to form the real image.

21. The gonioscopic viewing system according to claim 20, wherein the image is formed interior of the concave reflecting surface.

22. A viewing system for diagnosis or laser treatment of an interior structure of a patient's eye, comprising:

a first lens system including a concave posterior lens surface with a shape substantially corresponding to the shape of an average cornea so that, when placed on a patient's eye, light rays originating from the interior structure of the patient's eye and passing through the aqueous humor, pass through the cornea and the posterior lens surface of the first lens system and are directed by the first lens system toward an image forming system; and an image forming system optically aligned with the first lens system for capturing the light rays directed by the first lens system and including at least first and second light reflecting surface, one of which is curved, arranged optically in series for reflecting and focussing the captured light rays to form a real image of the interior structure outside of the patient's eye.

23. The viewing system according to claim 22, wherein the real image is an intermediate real image that is inverted and reversed, and the image forming system further includes a biconvex lens located anterior of the first and second reflecting surfaces for capturing and focussing the light rays forming the intermediate real image to form an upright and true real image of the interior structure of the patient's eye.

24. The viewing system according to claim 23, and further including a convex anterior lens surface following the first and second reflecting surfaces for bending the light rays toward the biconvex lens.

25. The viewing system according to claim 24, wherein the biconvex lens is spaced in a anterior direction from the convex anterior lens surface.

26. The viewing system according to claim 25, further comprising an intermediate meniscus shaped lens positioned between the convex anterior lens surface and the biconvex lens for further bending the light rays toward the biconvex lens.

27. The viewing system according to claim 23, wherein the one curved reflecting surface is a concave reflecting surface.

28. The viewing system according to claim 27, wherein the concave reflecting surface constitutes the first reflecting surface and is arranged to reflect the light rays in a posterior direction, and the second reflecting surface is disposed posterior of the concave reflecting surface for reflecting light rays from the concave reflecting surface in an anterior direction to form the intermediate real image.

29. The viewing system according to claim 28, wherein the second reflecting surface is planar.

30. The viewing system according to claim 28, wherein the second reflecting surface is concave.

31. The viewing system according to claim 28, wherein the first and second reflecting surfaces are symmetrically shaped.

32. The viewing system according to claim 28, wherein the biconvex lens has anterior and posterior surfaces which are partially mirrored for forming third and fourth reflecting surfaces for reflecting light from the intermediate real image to form the upright and true real image anterior of the biconvex lens.

33. The viewing system according to claim 32, wherein the third reflecting surface is a planar surface disposed in a central region of the anterior surface of the biconvex lens and the fourth reflecting surface is in a peripheral region of the posterior surface of the biconvex lens to form a ring defining an opening through which light exiting the first lens system passes toward the third reflecting surface.

34. The viewing system according to claim 33, wherein the fourth reflecting surface is a concave reflecting surface.

35. The viewing system according to claim 22, wherein the curved surface comprises an ellipsoidal reflecting surface for reflecting the light passing through the posterior lens surface of the first lens system generally toward a focus of the ellipsoidal surface to form a conjugate pupil region of the patient's eye, and the other reflecting surface comprises a parabolic reflecting surface for reflecting light emanating from the conjugate pupil region to form the real image.

36. The viewing system according to claim 22, wherein the other reflecting surface comprises a central convex reflecting surface and the one curved comprise a concave reflecting surface having a plus optical power disposed around the central convex reflecting surface for reflecting and focussing the light rays passing through the posterior lens surface of the first lens system toward the central convex reflecting surface which in turn reflects the focussed light to form the real image.

37. The viewing system according to claim 36, wherein the image is formed interior of the concave reflecting surface.

38. The viewing system according to claim 22, wherein the viewing system comprises gonioscopic viewing system for viewing the chamber angle of the patient's eye.

39. The viewing system according to claim 23, wherein the viewing system comprises an indirect ophthalmoscopic viewing system for viewing the fundus of the patient's eye.

* * * * *